United States Patent [19]

Hamill et al.

[11] Patent Number: 4,824,863
[45] Date of Patent: Apr. 25, 1989

[54] ANTIBIOTIC A80438

[75] Inventors: Robert L. Hamill, Greenwood; Walter M. Nakatsukasa, Indianapolis; Raymond C. Yao, Carmel, all of Ind.

[73] Assignee: Eli Lilly and Company, Indianapolis, Ind.

[21] Appl. No.: 738,320

[22] Filed: May 28, 1985

[51] Int. Cl.$^4$ .................... A61K 31/00; C07D 309/22
[52] U.S. Cl. ................................. 514/460; 549/353; 435/118; 514/23; 536/1.1; 536/16.8; 536/18.1
[58] Field of Search .............. 536/16.8, 18.1, 1.1; 514/25, 23, 460; 549/343

[56] References Cited

U.S. PATENT DOCUMENTS

| | | | |
|---|---|---|---|
| 3,839,557 | 10/1974 | Raun | 424/115 |
| 3,947,586 | 3/1976 | Messersmith | 424/283 |
| 3,950,514 | 4/1976 | Sawada | 424/121 |
| 4,061,775 | 12/1977 | McDougald | 424/263 |
| 4,218,438 | 8/1980 | Callender et al. | 424/115 |
| 4,263,427 | 4/1981 | Liu et al. | 536/1 |
| 4,278,663 | 7/1981 | Liu et al. | 536/16.8 |
| 4,366,168 | 11/1982 | Clinton et al. | 424/283 |
| 4,565,862 | 1/1986 | Foley et al. | 536/16.8 |
| 4,582,822 | 4/1986 | Hamill et al. | 536/16.8 |

OTHER PUBLICATIONS

Westley in "Polyether Antibiotics–Naturally Occurring Acid Ionophores," vol. 1, J. W. Westley, Ed., Marcel Dekker, New York, 1982, pp. 1, 11–12.
Taylor et al., ibid., pp. 103 and 109–110.
S. Omura et al., "Isolation of a New Polyether Antibiotic, Lonomycin," *J. Antibiotics* 29 (1), 15–20 (1976).
C. Riche et al., "Crystal and Molecular Structure of Emericid: A New Polyether Antibiotic," *J.C.S. Chem. Comm.* 1975, 951–952.
M. Ohshima et al., "Antibiotic DE-3936, A Polyether Antibiotic Identical with Lonomycin; Taxonomy, Fermentation, Isolation and Characterization," *J. Antibiotics* 29 (4), 354–365 (1976).
N. Tsuji et al., "Two New Antibiotics, A-218 and K-41; Isolation and Characterization," *J. Antibiotics* 29 (1) 10–14 (1976).

Primary Examiner—Johnnie R. Brown
Assistant Examiner—Elli Peselev
Attorney, Agent, or Firm—Nancy J. Harrison; Leroy Whitaker

[57] ABSTRACT

New polyether antibiotic A80438, its acyl and alkyl ester, alkyl ether and urethane derivatives, and salts thereof, are useful antibacterial and anticoccidial agents and increase feed-utilization efficiency in animals. Method of making A80438 by culture of *Streptomyces bobili* NRRL 15971 and synergistic compositions comprising (1) and A80438 compound and (2) nicarbazin, 4,4'-dinitrocarbanilide, certain napthalenamine and benzenamine compounds or metichlorpindol are also provided.

31 Claims, 2 Drawing Sheets

ANTIBIOTIC A80438

SUMMARY OF THE INVENTION

This invention relates to the new polyether antibiotic A80438 and to a new strain of *Streptomyces bobili*, NRRL 15971, which produces this antibiotic. The structure of A80438 is shown in formula 1:

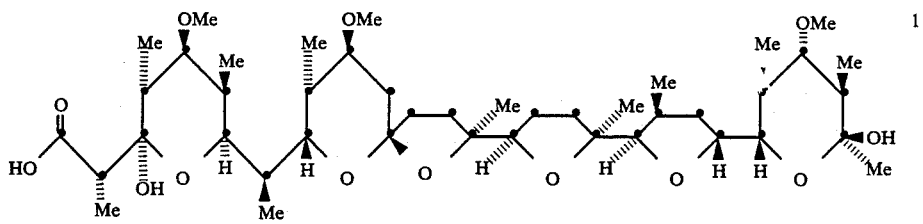

This invention also relates to acyl and alkyl ester and alkyl ether derivatives of A80438 and to the salts of A80438 and of the derivatives.

In addition, this invention provides A80438 urethane derivatives which are believed to have formula 2:

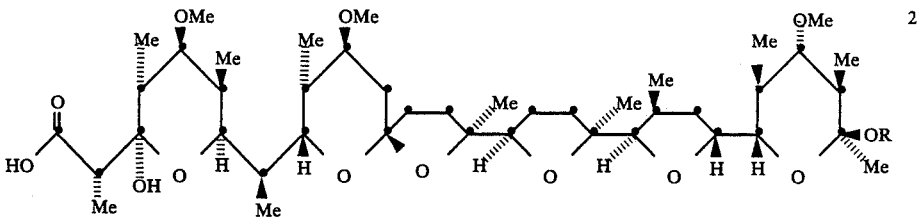

wherein R is —CONHR$_1$ and R$_1$ is alkyl, aryl, alkylaryl, arylalkyl, haloaryl, nitroaryl, haloarylalkyl, alkoxyaryl, aryloxyaryl, arylcycloalkyl, acylaryl and cycloalkyl; and salts of these derivatives.

Other aspects of this invention are methods of producing A80438 by culturing a novel strain of *Streptomyces bobili*, NRRL 15971, under submerged aerobic fermentation conditions until a substantial level of the antibiotic is produced. A80438 is extracted from the fermentation broth and from the mycelium with polar organic solvents. A80438 is separated and further purified by techniques such as column chromatography.

Because *Streptomyces bobili* NRRL 15971 is a newly discovered strain, this invention further provides a biologically purified culture of this microorganism.

A80438 is a useful antibacterial and anticoccidial agent. It improves feed-utilization efficiency in ruminants and acts as a growth promotant in ruminants and in monogastric animals. In addition, A80438 has insecticidal, inotropic and antiviral activity. Further, A80438 is useful as an ionophore. Methods and compositions pertaining to these uses are also provided.

This invention further relates to synergistic compositions of A80438, its acyl and alkyl ester, alkyl ether and urethane derivatives or a pharmaceutically acceptable salt thereof (an "A80438 compound"), together with a compound selected from nicarbazin, 4,4'-dinitrocarbanilide, metichlorpindol and certain naphthalenamine or benzenamine compounds. These compositions are useful in controlling coccidiosis in animals. Methods for using these compositions are another aspect of the invention.

DESCRIPTION OF THE DRAWINGS

The drawings show the following infrared absorption spectra in chloroform.

DETAILED DESCRIPTION OF THE INVENTION

Improved antibiotics continue to be needed in the veterinary field. Enhancing growth promotion in animals is one desired feature of such antibiotics. Growth promotion can be achieved by reducing disease and by increasing feed-utilization efficiency.

Coccidiosis is a serious problem for the poultry industry. Coccidiosis results from infection by one or more species of Eimeria or Isopora. Improved anticoccidial agents are in demand because of the continuing economic losses due to coccidiosis.

Promoting growth by increasing feed-utilization efficiency is another ecomonically desirable objective of veterinary science. Of particular interest is growth promotion in ruminants, such as cattle.

The mechanism for utilizing the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA).

The relative efficiency of VFA utilization is connected to overall efficiency. Thus, although acetates and butyrates are used, propionates are used with greater efficiency. Also, the fermentation efficiency of propionate production is greater than that of butyrate or acetate. This is in addition to the utilization efficiency. A beneficial compound, therefore, stimulates animals to produce a higher proportion of propionates from carbohydrates, thereby increasing carbohydrate-utilization efficiency.

A80438 is a new member of the group of polyether antibiotics. Westley (John W. Westley, "Polyether Antibiotics: Naturally Occurring Acid Ionophores, Vol. 2, Chemistry," Marcel Dekker, New York, 1983) has separated existing polyethers by class and type. Using Westley's system, A80438 is a new member of the Class 1a, type (2), group of polyethers. Examples of other members of this group are: lonomycin (also called emericid, A218, RP 31559 and DE 3936; see U.S. Pat. No. 3,950,514), monensin (U.S. Pat. No. 3,501,568), nigericin and laidlomycin.

Characteristics of A80438

Figure 1:
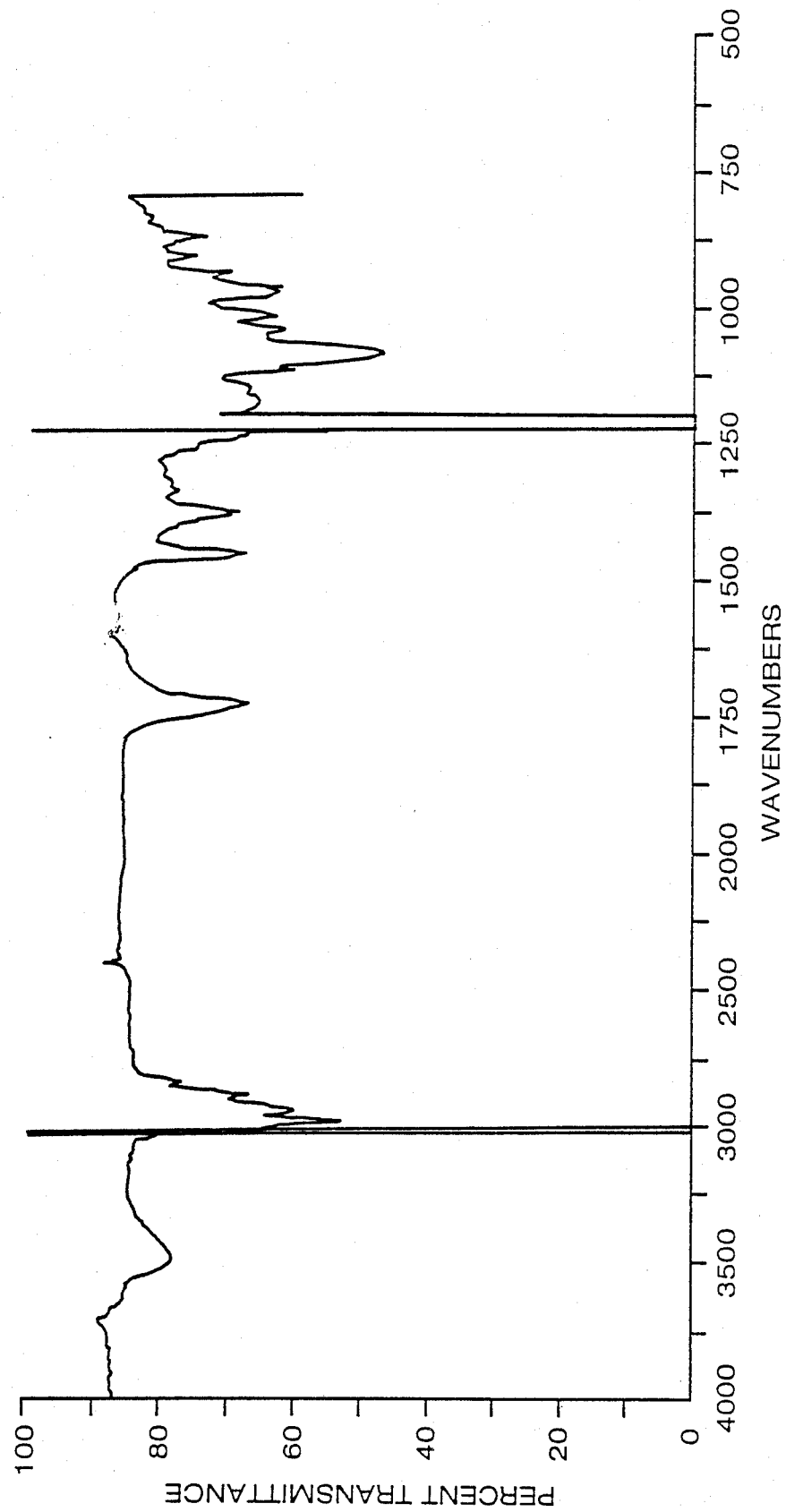
FIG. 1: A80438 (acid form)
Figure 2:
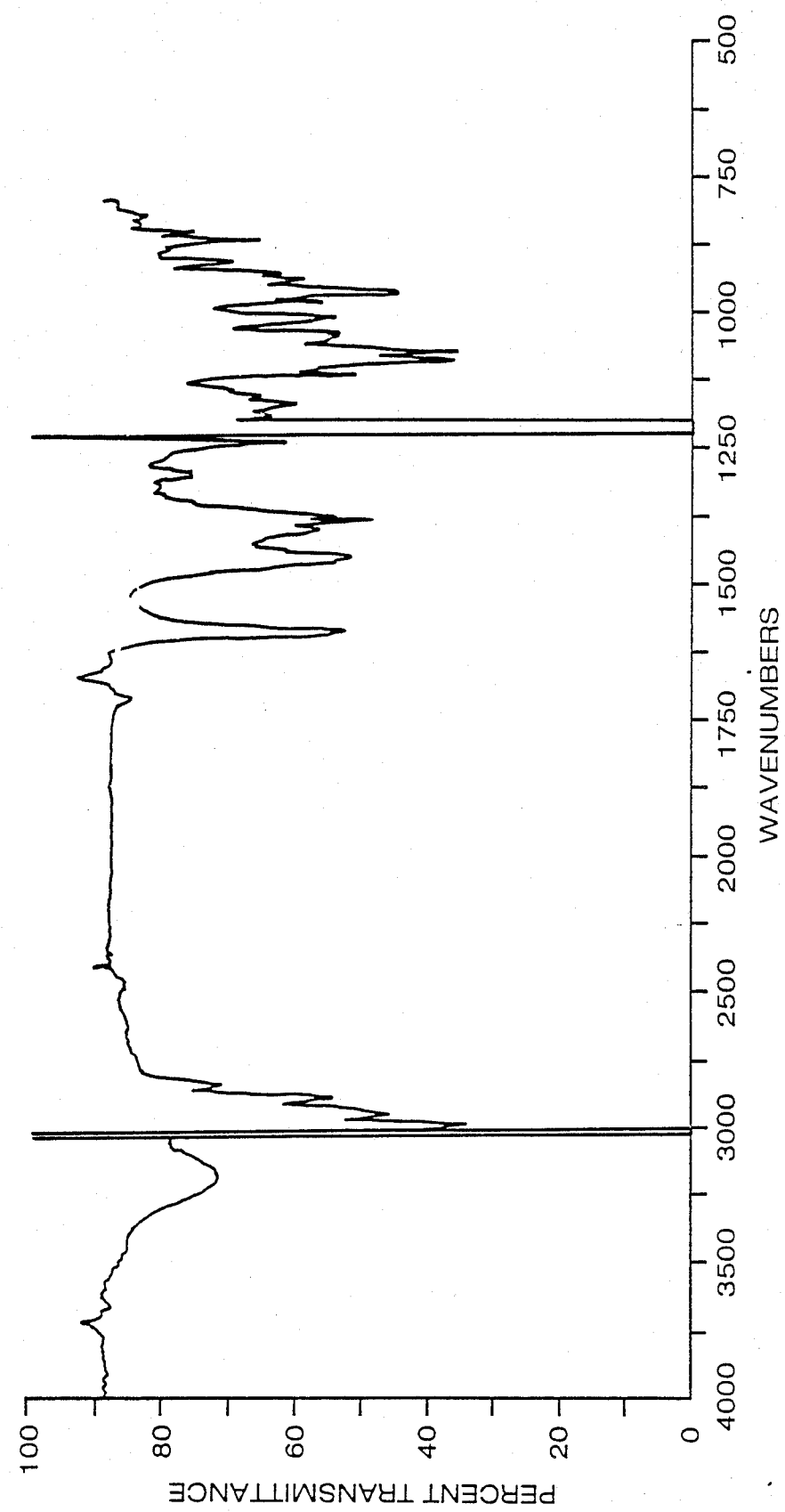
FIG. 2: A80438 (Na Salt)

A80438 (in its sodium salt form) has the following characteristics:
State: white crystals (from acetone-water)
mp: 160°–162° C.
pKa: =5.2 (66% aqueous dimethylformamide)
$[\alpha]^{25}D$: +102° (c 1, CHCl$_3$)
Molecular weight: 820 by field desorption mass spectrometry (FDMS)
Empirical formula: C$_{43}$H$_{74}$O$_{13}$Na
UV: no absorbance
IR (acid form, CHCl$_3$): 3018, 2976, 2940, 1731, 1457, 1379, 1206, 1118, 1088, 1041, 1021, 978, and 968 cm$^{-1}$ (see FIG. 1)
IR (Na salt, CHCl$_3$): 3018, 2979, 2938, 2881, 2832, 1710, 1591, 1454, 1387, 1306, 1243, 1215, 1170, 1117, 1089, 1076, 974, 967 and 874 cm$^{-1}$ (see FIG. 2)
Solubility: Not very soluble in water; soluble in dimethyl sulfoxide, dimethylformamide, lower alcohols such as methanol, ketones such as acetone, esters such as ethyl acetate, halogenated hydrocarbons such as chloroform and hydrocarbons such as diethyl ether, benzene, toluene and warm hexane.

Based on its physical characteristics A80438 is believed to have the structure shown in formula 1. As is apparent from its structure, A80438 has an acid function capable of forming salts and ester derivatives. A80438 also has at least one hydroxyl group which can be esterified or which can form ether derivatives. The acyl and alkyl ester, the alkyl ether and the urethane derivatives of A80438, and the pharmaceutically-acceptable salts of A80438 and of these derivatives are also useful as antibiotics and as agents which increase feed-utilization efficiency.

The term "acyl" means a C$_1$ to C$_7$, preferably a C$_1$ to C$_4$, alkanoic acid moiety, i.e., a radical of the formula

wherein R$_{1a}$ is C$_1$ to C$_6$-alkyl or hydrogen, e.g., acetyl, propionyl, butyryl and the like.

The term "cycloalkyl" means cyclic hydrocarbon groups containing from 3 to 7 carbon atoms, such as, cyclopropyl, cyclobutyl, cyclohexyl and the like, cyclohexyl being preferred. The cycloalkyl group may be substituted by an aryl residue, as defined herein, to form an arylcycloalkyl residue, e.g., 2-(phenyl)cyclopropyl.

The term "alkoxy" means a C$_1$ to C$_7$ lower alkyl group having an oxygen function substituted therein, such as, methoxy, ethoxy, propoxy and the like.

The term "aryl" denotes an aromatic residue derived by the removal of a hydrogen atom from an aromatic hydrocarbon, such as, for example, phenyl, pyridyl or furyl, especially phenyl. The "aryl" residue may be substituted by various groups. A substituent on a phenyl nucleus is preferably on the 4-position. Examples are 4-alkylaryl, e.g., 4-methylphenyl (4-tolyl); 4-halophenyl, e.g., 4-chlorophenyl; 4-nitrophenyl; 4-aryloxy-aryl, e.g., 4-phenoxyphenyl; 4-alkoxyphenyl, e.g., 4-methoxyphenyl; and 4-(alkyl-carbonyl)phenyl, e.g., 4-(methylcarbonyl)phenyl or 4-(phenylcarbonyl)phenyl.

The term "alkyl" means a C$_1$ to C$_7$ straight or branched chain hydrocarbon, preferably a C$_1$ to C$_4$ hydrocarbon, e.g., methyl, ethyl, propyl, isopropyl, n-butyl, etc. The alkyl group may be substituted by an aryl residue, as defined supra, to form an arylalkyl residue, e.g., phenylethyl or 2-phenylethyl or by a haloaryl residue to form a haloarylalkyl residue, e.g., 4-bromophenethyl.

The term "an A80438 compound" is used herein to designate antibiotic A80438 (formula 1), an acyl or alkyl ester or an alkyl ether derivative of antibiotic A80438, a urethane derivative of antibiotic A80438 (formula 2) or a pharmaceutically acceptable salt of antibiotic A80438 or of its acyl or alkyl ester, alkyl ether or urethane derivatives.

Antibiotic A80438 is produced by an A80438-producing strain of (1) the *Streptomyces bobili* NRRL 15971 culture described herein or (2) a *Streptomyces pactum* culture, NRRL 15970, which is described by Robert L. Hamill and Raymond C. Yao in their copending application entitled PROCESS FOR PRODUCING ANTIBIOTIC A80438, Ser. No. 06/738,317, filed herewith this even date. The antibiotic is produced under submerged aerobic conditions in a suitable culture medium; it can be recovered from the culture medium by using various isolation and purification procedures understood in the art.

Cultures of the two A80438-producing organisms have been deposited and made part of the stock culture collection of the Midwest Area Northern Regional Research Center, Agricultural Research Service, U.S. Department of Agriculture, 1815 North University Street, Peoria, Ill. 61604, from which they are available to the public under the accession numbers NRRL 15971 (the *S. bobili* strain) and NRRL 15970 (the *S. pactum* strain).

The new *Streptomyces bobili* strain which is useful for the preparation of antibiotic A80438 was isolated from a soil sample from Scotland. For convenience in describing the *S. bobili* strain, it is called the A80438 culture.

Taxonomic studies of this organism were carried out by Frederick P. Mertz of the Lilly Research Laboratories. Based on these studies, the organism is classified as a new strain of *Streptomyces bobili* (Waksman and Curtis 1916) Waksman and Henrici 1948. This classification is based on an examination of published descriptions of this species [R. E. Buchanan, and N. E. Gibbons (eds), "Bergey's Manual of Determinative Bacteriology", 8th Edition, The Williams and Wilkins Co., Baltimore, 1974; E. G. Shirling, and D. Gottlieb, "Cooperative Description of Type Cultures of Streptomyces", *Int. J. Syst. Bacteriol.* 18(4): 279–399 (1968); and S. A. Waksman, "The Actinomycetes Vol. II", The Williams and Wilkins Co., Baltimore, 1961].

Methods Used

The methods recommended by the International Streptomyces Project (ISP) for the characterization of Streptomyces species [E. B. Shirling and D. Gottlieb, "Methods for Characterization of Streptomyces Species", *Int. J. Syst. Bacteriol.* 16(3), 313–340 (1966)] have been followed along with certain supplementary tests [D. Berd, "Laboratory Identification of Clinically Important Aerobic Actinomycetes", *Appl. Microbiol.*

25(4), 665–681 (1973); and D. J. Blazevic and G. M. Ederer, "Principles of Biochemical Tests in Diagnostic Microbiology", John Wiley and Sons, Inc., New York, 1975, p. 136].

Carbon utilization was determined on ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 which has tyrosine removed.

Starch hydrolysis was determined by testing for the presence of starch with iodine on ISP No. 4 (inorganic salts-starch agar) plates (see Blazevic and Ederer, supra).

Morphology was studied using an optical light microscope. A scanning electron microscope (SEM) was used to study the spore surface ornamentation.

NaCl tolerance was measured by adding NaCl to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Color Standards Department, Container Corporation of America, Chicago, Ill., 1958) were used to assign color names.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates", Appl. Microbiol. 12, 421–423 (1964)] and of Lechevalier [M. P. Lechevalier, "Identification of Aerobic Actinomycetes of Clinical Importance", J. Lab. Clin. Med. 71, 934–944 (1968)].

Resistance to lysozyme was measured by methods recommended by Gordon and Barnett [R. E. Gordon and D. A. Barnett, "Resistance to Rifampin and Lysozyme of Strains of Some Species of Mycobacterium and Nocardia as a Taxonomic Tool", Int. J. Syst. Bacteriol. 27, 176–178 (1977)].

Resistance to antibiotics was measured by padding antibiotic sensitivity discs onto the surface of seeded ISP No. 2 agar plates.

Phosphatase and urease were determined by methods described by Blazevic and Ederer, supra.

Cultural Characteristics

The organism has very limited growth on both complex and chemically defined media. From a total of 15 agar culture media, only 5 support good growth, 4 support minimal growth, and the remaining 6 do not support any growth. ISP media Nos. 2, 5 and 7, Emerson's agar, and yeast-dextrose agar support good growth. Aerial mycelia are not produced. Coremia are formed abundantly. The limited growth ability and the abundant formation of coremia are distinctive features of this culture. The coremia, which macroscopically resemble poorly developed secondary growth, have a reddish color. The nearest matching color tab in the Tresner and Backus System [H. D. Tresner and E. J. Backus, "System of Color Wheels for Streptomycete Taxonomy," Appl. Microbiol. 11: 335–338 (1956)] is 5 cb grayish yellowish pink.

The reverse side of the colony is reddish orange to a light yellowish brown. No soluble pigments are produced. These cultural features are best demonstrated on ISP medium No. 7 (tyrosine agar). Table I presents these cultural characteristics.

TABLE I

Cultural Characteristics of A80438[a]
Agar Medium Characteristic[b]

| | | |
|---|---|---|
| ISP No. 2 | G: | Good |
| | R: | 76.1.y Br |
| | C: | Poor: 5 cb g.y Pink |
| | Sp: | None |
| ISP No. 5 | G: | Abundant |
| | R: | 39. gy.rO |
| | C: | Good: 5 gc 1.rBr |
| | Sp: | Very light reddish brown |
| ISP No. 7 | G: | Good |
| | R: | 39. gy.rO |
| | C: | Good: 5 cb g.y Pink |
| | Sp: | None |
| Emerson | G: | Good |
| | R: | 76.1. yBr |
| | C: | Good: 5 cb g.y Pink |
| | Sp: | None |
| Yeast-dextrose | G: | Abundant |
| | R: | 79. 1.gy.y Br |
| | C: | None |
| | Sp: | None |

[a]On Czapek's, glycerol-glycine and potato-carrot agars, growth was poor; on ISP 3, 4, tap water, Anio-Hensens, glucose-asparagine, and tomato-paste-oatmeal agars, there was no growth.
[b]G = Growth; R = Reverse; C = Coremia; Sp = Soluble pigment.

Morphological Characteristics

A80438 does not produce sporophores. The presence of coremia represents a special morphological characteristic. The coremia are fibrous, abundant, and readily observed with both light and electron microscopes.

Physiological Characteristics

Analysis of hydrolyzed whole cells indicates that LL-DAP is present, but the meso isomer is not present. Arabinose, glucose, rhamnose, and ribose are the sugar components. The cell wall is type I. Arabinose is normally not present in Streptomyces cell walls. However, Pridham (T. G. Pridham and A. J. Lyons, Jr, "Progress in Clarification of the Taxonomic and Nomenclatural Status of Some Problem Actinomycetes", in "Developments in Industrial Microbiology, Vol. 10", American Institute of Biological Sciences, Washington, D.C., 1969) lists several species where arabinose was found. The cell-wall sugar pattern is classified "NC" (no characteristic sugar). Culture A80438 belongs to the genus Streptomyces; however, it is not a typical taxon of this genus.

The carbon-utilization pattern for A80438 is as follows: adonitol, cellobiose, D-fructose, D-galactose, D-glucose, i-inositol, D-lactose, D-melezitose, D-melibiose, raffinose, L-rhamnose, ribose, sucrose, trehalose and D-xylose are utilized for growth. L-Arabinose, cellulose, dextran, inulin, mannitol, D-mannose, salicin and xylitol do not support growth.

Culture A80438 is resistant to cephalothin (30 $\mu$g), lincomycin (2 $\mu$g) and penicillin G (10 units). It is sensitive to bacitracin (10 units), gentamicin (10 $\mu$g), neomycin (30 $\mu$g), oleandomycin (15 units), rifampin (5 $\mu$g), streptomycin (10 $\mu$g), tetracycline (30 $\mu$g), tobramycin (10 $\mu$g), vancomycin (30 $\mu$g) and lysozyme.

Culture A80438 is Gram positive, and nonacid fast. It does not hydrolyse or peptonize skim milk, and does not liquefy gelatin. It reduces nitrate to nitrites in organic nitrate broth (ISP 8), tolerates up to 4 percent NaCl, and grows at temperatures between 10° and 42° C. It does not survive when exposed to 50° C. for 8 hours.

Melanoid pigments are not produced when A80438 is grown in ISP 1 (tryptone-yeast extract broth) or on slants of ISP 6 (peptone-yeast extract-iron agar) or ISP 7 (tyrosine agar).

A80438 produces catalase, phosphatase and urease.

Culture A80438 decomposes casein, DNA, esculin, hypoxanthine, tyrosine and xanthine. It does not decompose calcium malate, chitin, elastin, guanine, hippurate, keratin or starch.

Species Determination

Cultural, morphological, and physiological characteristics of strain A80438 were compared with the published descriptions of similar species. The following five species resemble A80438:

Streptomyces aerocolonigenes[a]
Streptomyces bobili[a]
Streptomyces glomeroaurantiacus[b]
Streptomyces vendargenesis[c]
Streptomyces verne[c]

[a]Shirling and Gottlieb, 1968, supra.
[b]E. B. Shirling and D. Gottlieb, "Cooperative Description of Type Cultures of Streptomyces", *Int. J. Syst. Bacteriol.* 22(4), 265-394 (1972).
[c]E. B. Shirling and D. Gottlieb, "Cooperative Description of Type Cultures of Streptomyces", *Int. J. Syst. Bacteriol.* 19(4), 375-390 (1969).

These five cultures are reported in the literature as being devoid of aerial mycelia, not producing melanoid pigments, having a similar carbon utilization pattern, and having other cultural and physiological properties in common with A80438.

Of the five cultures, *S. bobili* has more characteristics in agreement with A80438. In addition, only *S. bobili* and *S. glomeroaurantiacus* are listed as validly published in the Approved Lists of Bacterial Names [V. B. D. Skerman et al., "Approved Lists of Bacterial Names", *Int. J. Syst. Bacteriol.* 30(1), 225-420 (1980)].

*S. bobili* is similar to A80438 culturally and physiologically. Culturally, neither produces aerial mycelia or soluble pigments. Both have a rather distinctive reddish-orange pigment on the reverse side of the colony. Since neither culture produces aerial mycelia, morphological comparisons cannot be made. A80438 produces coremia. The published descriptions of *S. bobili* do not mention these structures. Because Waksman, supra, states that "coremia formation is of no taxonomic significance", this distinguishing feature of A80438 was not greatly emphasized.

Physiological characteristics shared by A80438 and *S. bobili* are: reduction of nitrate, absence of melanoid pigmentation, toleration of 4 percent NaCl, inhibition by streptomycin, and a similar carbon-utilization pattern. The similarities and differences between A80438 and *S. bobili* are summarized below:

| Similarities | Differences |
| --- | --- |
| Absence of aerial mycelium | Gelatin liquefaction |
| Absence of melanoid pigments | Growth on Czapek's agar |
| Absence of soluble pigments | Growth on glucose-asparagine agar |
| Carbon-utilization pattern | Hydrolysis of starch |
| Color of reverse side | Peptonization of milk |
| Inhibition by streptomycin | Reverse color pH indicator |
| NaCl tolerance | |
| Nitrate reduction | |

Table II gives a detailed comparison of the characteristics of A80438 and *S. bobili.*

TABLE II

Comparison of the Characteristics of A80438 and *Streptomyces bobili*[a]

| Characteristic | A80438 | S. bobili |
| --- | --- | --- |
| Aerial mycelium | − | − |
| Gelatin liquefaction | − | + |
| Growth on Czapek's agar | trace | abundant |
| Growth on glucose-asparagine agar | − | + |
| Melanoid pigmentation | − | − |
| NaCl tolerance-percent | 4 | 4 |
| Nitrate reduction | + | + |
| Peptonization of skim milk | − | + |
| Reverse color a pH indicator | − | + |
| Reverse side color | reddish-orange | reddish-orange |
| Soluble pigment | − | − |
| Starch hydrolysis | − | + |
| Streptomycin inhibition | + | + |
| Utilization of: | | |
| L-arabinose | − | + |
| D-fructose | + | + |
| D-galactose | + | + |
| D-glucose | + | + |
| i-inositol | + | + |
| D-lactose | + | + |
| mannitol | − | − |
| raffinose | + | + |
| L-rhamnose | + | + |
| salicin | − | − |
| sucrose | + | + |
| D-xylose | + | + |

[a] + = Positive reaction
− = negative reaction

These comparisons demonstrate that A80438 is similar to *S. bobili.* The differences are not considered sufficient to erect A80438 as a new taxon. Therefore, culture A80438 is classified as a strain of *Streptomyces bobili* (Waksman and Curtis 1916) Waskman and Henrici 1948.

As is the case with other organisms, the characteristics of the A80438-producing culture *Streptomyces bobili* NRRL 15971 are subject to variation. Recombinants, mutants or variants of the strain may be obtained by methods known in the art. For example, mutants can be obtained by treatment with various known physical and chemical mutagens such as ultraviolet light, X rays, gamma rays and chemicals such as N-methyl-N-'-nitro-N-nitrosoguanidine. All natural and induced variants, mutants and recombinants of this *Streptomyces bobili* strain which retain the characteristic of A80438 production are part of this invention.

The culture medium used to grow *Streptomyces bobili* NRRL 15971 or *Streptomyces pactum* NRRL 15970 can be any one of a number of media. For economy in production, optimal yield, and ease of product isolation, however, certain culture media are preferred. For example, for *S. bobili* a preferred carbohydrate source in large-scale fermentation is glucose, although ribose, xylose, fructose, galactose, potato dextrin and the like can also be used. Glucose is also a preferred carbohydrate source for *S. pactum,* although sucrose, fructose, blackstrap molasses, starch and the like can also be used.

A preferred nitrogen source for both *S. bobili* and *S. pactum* is enzyme-hydrolyzed casein. Another preferred nitrogen source for *S. pactum* is meat peptone. Other nitrogen sources such as fish meal, liver meal, and the like should also be useful nitrogen sources.

Among the nutrient inorganic salts which may advantageously be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 ml/L) of an antifoam agent such as polypropylene glycol may be added to large scale fermentation media if needed.

For production of substantial quantities of antibiotic A80438, submerged aerobic fermentation in tanks is preferred. Small quantities of A80438 may be obtained by shake-flask culture. Because of the time lag in antibiotic production commonly associated with inoculation of large tube tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80438 is produced by *Streptomyces bobili* or *Streptomyces pactum* when grown at temperatures between about 25° and about 37° C. A good temperature for A80438 production appears to be about 30° C.

As is customary in submerged aerobic culture processes, sterile air is blown into the vessel from the bottom while the medium is stirred with conventional turbine impellors. Under the conditions used thus far, the maximum oxygen uptake of the fermentation does not exceed about 0.2 mM/L/minute. In a fully baffled 165-liter fermentor containing approximately 115 liters of broth, an aeration rate of 0.125 v/v/m with an agitation rate of 150–200 rpm is sufficient to maintain the level of dissolved oxygen at or above 30% of air saturation.

Production of antibiotic A80438 can be followed during the fermentation by testing samples of the broth for antibiotic activity against organisms known to be sensitive to the antibiotic. One assay organism useful in testing A80438 is *Bacillus subtilis* ATCC 6633. The bioassay is conveniently performed by the agar-well plate test.

Following its production under submerged aerobic fermentation conditions, A80438 can be recovered from the fermentation medium by methods used in the fermentation art. The antibiotic activity produced during fermentation of the A80438-producing organism occurs both in the filtered broth and in the mycelial mass. Maximum recovery of A80438 is accomplished, therefore, by initially filtering the medium to separate the broth from the mycelial mass. The filtered broth and the mycelial mass can then be purified separately to give their respective portion of A80438. A variety of techniques may be used in this purification.

A preferred technique for purification of the filtered broth involves adjusting it to a pH of about 9 and extracting with a suitable solvent such as, for example, ethyl acetate. The extracting solvent can then be evaporated under vacuum to give the broth portion of A80438.

A preferred method of purifying the mycelial mass is to extract the separated mycelial filter cake with a suitable solvent such as, for example, methanol. The extracting solvent is then evaporated under vacuum to give a concentrated aqueous solution. This aqueous solution is then adjusted to a pH of about 9 and is extracted with a suitable solvent such as, for example, ethyl acetate. The extracting solvent is then concentrated under vacuum to give the mycelial portion of A80438.

The broth and mycelial portions of the A80438 complex are further purified by similar procedures. A preferred procedure involves silica gel chromatography.

Separation of antibiotic A80438 can be followed by thin-layer chromatography (TLC) or high performance liquid chromatography (HPLC). One convenient silica gel TLC solvent system is toluene:ethanol (4:1). The antibiotic can be detected by bioautography using, for example, *Bacillus subtilis* or by other methods such as, for example, vanillin-sulfuric acid spray reagent.

Alternatively, the culture solids, including medium constituents and mycelium can be used without extraction or separation, but preferably after removal of water, as a source of A80438. For example, after production of A80438, the whole fermentation broth can be dried by lyophilization, by drum-drying, or by azeotropic distillation and drying. The dried broth is then mixed directly into feed premix.

The salts of A80438 and of its derivatives are useful for separating and purifying the antibiotics. The pharmaceutically-acceptable salts are particularly useful. Examples of salts are the alkali-metal, alkaline-earth-metal and amine salts of A80438 and of its derivatives.

Representative and suitable alkali-metal and alkaline-earth metal salts of A80438 include the sodium, potassium, lithium, cesium, rubidium, barium, calcium and magnesium salts. Suitable amine salts of A80438 include the ammonium and the primary, secondary, and tertiary $C_1$–$C_4$-alkylammonium and hydroxy-$C_2$–$C_4$-alkylammonium salts. Illustrative amine salts include those formed by reaction of A80438 with ammonium hydroxide, methylamine, sec-butylamine, isopropylamine, diethylamine, di-isopropylamine, ethanolamine, triethylamine, 3-amino-1-propanol and the like.

It is well known in the veterinary pharmaceutical art that the form of an antibiotic is not ordinarily of great significance when treating an animal with the antibiotic. In most cases, conditions within the animal change the drug to a form other than that in which it was administered. The salt form in which it may be administered is, therefore, not of great significance. The salt form may, however, be chosen for reasons of economy, convenience, and toxicity.

The alkali-metal and alkaline-earth-metal cationic salts of A80438 are prepared according to procedures commonly used for the preparation of cationic salts. For example, the free acid form of A80438 is dissolved in a suitable solvent such as acetone; about ½ volume of water is added and this solution is adjusted to a pH of about 9 to 10 with the base of the desired cationic salt (e.g. NaOH, KOH). The salt thus formed can be isolated by routine methods, such as filtration or evaporation of the solvent.

A preferred method of forming salts is to dissolve A80438 (acid form) in a water-immiscible solvent such as ethyl acetate, add an equal volume of water; adjust the mixture to pH 10 with the corresponding cationic base (e.g. NaOH, KOH, etc.). The separated organic phase is washed with water and concentrated to dryness. The residue is lyophilized from dioxane. The salt can be crystallized from an appropriate solvent, such as pentane.

The salts formed with organic amines can be prepared in a similar manner. For example, the gaseous or liquid amine can be added to a solution of A80438 in a suitable solvent such as acetone; the solvent and excess amine can be removed by evaporation.

A80438 acyl-ester derivatives are prepared by treating A80438 with a corresponding acid anhydride or acid chloride. Esterification occurs at one of the A80438 hydroxyl groups. Such esters are typically prepared by reacting A80438 with, for example, the corresponding acid anhydride at room temperature.

A80438 alkyl ester derivatives are prepared by esterification of the carboxyl group, using standard procedures. The A80438 alkyl ester derivatives are typically less active in vitro. When administered to an animal, however, such esters can act as pro drugs which are converted to A80438 in vivo.

The alkyl ether derivatives of A80438 are those compounds wherein one or more of the hydroxyl groups has been replaced by a YR group wherein:

Y represents O or S; and
R represents
  $C_1$–$C_6$-alkyl,
  $C_1$–$C_4$-alkoxy-$C_2$–$C_5$-alkyl,
  $C_1$–$C_4$-alkoxycarbonyl-$C_2$–$C_5$-alkyl,
  amino-$C_2$–$C_5$-alkyl,
  mercapto-$C_2$–$C_5$-alkyl,
  hydroxyalkyl,
  haloalkyl, or
  $(R')_m$-phenyl$(CH_2)_n$—,
    wherein
    R' represents $C_1$–$C_4$-alkyl, $C_1$–$C_4$-alkoxy, or hydroxy
    m represents 0–2; and
    n represents 0–3.

The terms alkyl and alkoxy have the meaning discussed supra, but are limited to the number of carbon atoms specified.

The term "hydroxyalkyl" refers either to a monohydroxy-$C_2$–$C_5$-alkyl moiety or, when Y is O, to the 2,3-dihydroxyprop-1-yl moiety.

The term "haloalkyl" refers to a $C_2$–$C_5$-alkyl moiety having from one to three halogen substituents, selected from the group consisting of bromine, chlorine, and fluorine. When the alkyl moiety is dihalo- or trihalo-substituted, the halo-substituents must be the same halogen moiety.

Preferred A80438 ether derivatives are those compounds wherein Y represents O and R represents $C_1$–$C_6$-alkyl. The ether derivatives are prepared by reacting A80438, or a salt thereof, with a corresponding primary alcohol or thiol.

With some of the starting alcohols or thiols it may be necessary to add an acid catalyst to the reaction. Suitable catalysts include hydrochloric acid, sulfuric acid, perchloric acid, methanesulfonic acid, benzenesulfonic acid, toluenesulfonic acid, selenium dioxide, and boron trifluoride.

A solvent such as, for example, water, acetone, benzene, ether, tetrahydrofuran, or dioxane may be added to facilitate the reaction. Reactions generally occur at room temperature, although higher temperatures may be used.

Although ordinary reaction work-up procedures are sometimes sufficient, additional purification may be required to obtain the compounds of this invention. Such purification may be accomplished by well-known methods, such as, for example, column chromatography, thin-layer chromatography, fractional crystallization and the like.

The A80438 urethane derivatives of formula 2 can be prepared by treating A80438 or an A80438 salt with an isocyanate of formula 3

$$R\text{—}NCO \qquad 3$$

wherein R is as defined supra.

Preferably, a salt of A80438, in particular the sodium salt, is used. The isocyanate of formula 3 should be added in slight excess, e.g., about 10% excess, in order to form the mono derivative in optimum quantity. The reaction is preferably carried out in an inert solvent such as a chlorinated hydrocarbon, e.g., carbon tetrachloride, methylene chloride or chloroform, ether, ethyl acetate or in an aromatic hydrocarbon solvent such as benzene or toluene. The reaction temperature is not critical but can be between above 0° C. and the boiling point of the reaction mixture, but is preferably about room temperature.

The A80438 compounds inhibit the growth of bacteria and fungi which are pathogenic to animal and plant life. For example, Table III shows the inhibitory concentration (MIC) at which A80438 inhibits certain organisms. The NMC's in Table III were determined by conventional agar-dilution assays.

TABLE III

| Antibacterial Activity of A80438 (Na salt) | |
|---|---|
| Test Organism | MIC (mcg/mL) |
| Staphylococcus aureus X1.1 | 0.5 |
| Staphylococcus aureus V41 | 0.5 |
| Staphylococcus aureus X400 | 0.5 |
| Staphylococcus aureus S13E | 0.5 |
| Staphylococcus epidermidis EPI1 | 0.5 |
| Staphylococcus epidermidis 222 | 0.25 |
| Streptococcus pyogenes C203 | 0.25 |
| Streptococcus pneumoniae Park1 | 0.125 |
| Streptococcus pneumoniae X66 | 0.5 |
| Streptococcus pneumoniae 2041 | 0.5 |
| Pseudomonas aeruginosa X528 | 64.0 |
| Shigella sonnei | 16.0 |
| Other Gram-negative bacteria tested | >128 |

The A80438 compounds also are active against anaerobic bacteria. Table IV shows the MIC's at which A80438 inhibits various anaerobic bacteria, as determined by standard agar-dilution assay. End points were read after 24-hour incubation.

TABLE IV

| Susceptibility of Anaerobic Bacterial Isolates to A80438 (Na salt) | |
|---|---|
| Anaerobic Bacteria | MIC (mcg/mL) |
| Clostridium difficile 2994 | 1 |
| Clostridium perfringens 81 | 1 |
| Clostridium septicum 1128 | 1 |
| Eubacterium aerofaciens 1235 | 1 |
| Peptococcus asaccharolyticus 1302 | <0.5 |
| Peptococcus prevoti 1281 | 8 |
| Peptostreptococcus anaerobius 1428 | 8 |
| Peptostreptococcus intermedius 1624 | 1 |
| Propionibacterium acnes 79 | 8 |
| Bacteroides fragilis 111 | 16 |
| Bacteroides fragilis 1877 | 16 |
| Bacteroides fragilis 1936B | 16 |
| Bacteroides thetaiotaomicron 1438 | 8 |
| Bacteroides melaninogenicus 1856/28 | 16 |
| Bacteroides melaninogenicus 2736 | 8 |
| Bacteroides vulgatis 1211 | 4 |
| Bacteroides corrodens 1874 | 16 |
| Fusobacterium symbiosum 1470 | 2 |

TABLE IV-continued

| Susceptibility of Anaerobic Bacterial Isolates to A80438 (Na salt) | |
|---|---|
| Anaerobic Bacteria | MIC (mcg/mL) |
| *Fusobacterium necrophorum* 6054A | 8 |

The acute toxicity of A80438 in mice, when administered by intraperitaneal injection and expressed as $LD_{50}$, was 8.84 mg/kg.

Anticoccidial activity is an important property of the A80438 compounds. Table V summarizes the results of two in vitro tissue-culture tests in which A-80438 inhibited *Eimeria tenella*.

TABLE V

| Activity of A80438 (Na salt) vs. *Eimeria tenella* In Vitro | | | | | |
|---|---|---|---|---|---|
| | Concentration (mcg/mL) | | | | |
| | 5 | 1 | 0.2 | 0.04 | 0.008 |
| Test 1 | C[a] | C | C-A | A | A |
| Test 2 | C | C | C-A | A | A |

[a]C = cytotoxic
A = active

Table VI summarizes the results of a study of the effect of A80438 in controlling an *Eimeria tenella* infection in chickens. In this study, groups of five 7-day-old chicks were fed a mash diet containing the antibiotic. After having been on this ration for 48 hours, each bird was inoculated with sporulated oocysts of *E. tenella*. Two other groups of five 7-day-old chicks were fed a mash diet which did not contain A80438. One of these groups was also inoculated with *E. tenella* after 48 hours (the infected controls). The other group was not inoculated with *E. tenella* (the normal controls). Results were evaluated seven days after inoculation. The birds were weighed, sacrificed, and examined for evidence of coccidial lesions. Coccidial involvement was measured on a scale of 0 (no evidence of coccidiosis) to 4 (maximum involvement for the Eimeria species). The percent reduction in lesion score was calculated by subtracting the average lesion score of the treated group from the average lesion score of the infected control group, dividing this difference by the average lesion score of the infected control group and multiplying by 100. The percent weight gain was calculated using the weight gain of normal controls as 100%.

TABLE VI

| | Activity of A80438 (Na Salt) vs. *Eimeria tenella* in vivo | | | |
|---|---|---|---|---|
| ppm in Diet | Percent Mortality | Percent Weight Gain | Percent Reduction in Lesion Scores | |
| | | | Intestinal | Cecal |
| 35 | 0.0 | 93 | 64 | 37 |
| 70 | 0.0 | 92 | 95 | 75 |
| Infected Controls | 0.0 | 79 | 0 | 0 |
| Normal Controls | 0.0 | 100 | — | — |

For treating coccidiosis in poultry, a non-toxic anticoccidial amount of an A80438 compound is administered to infected or susceptible birds, preferably orally on a daily basis. The A80438 compound can be supplied in many ways, but it is most conveniently supplied with a pharmaceutically acceptable carrier, preferably the feed ingested by the birds. Although a variety of factors must be considered in determining an appropriate concentration of A80438 compound, the rates of administration are generally in the range of about 2 to about 100 ppm in the feed and are preferably in the range of about 25 to about 75 ppm of feed ration.

In another aspect, this invention relates to compositions for treating coccidiosis in poultry containing an A80438 compound. One group of these are compositions comprising an effective amount of an A80438 compound for treating coccidiosis together with a suitable vehicle. Another group of these are compositions comprising an effective amount of:
(1) an A80438 compound; in combination with
(2) a compound selected from the group consisting of
(a) nicarbazin,
(b) 4,4'-dinitrocarbanilide,
(c) a naphthalenamine compound of formula 4:

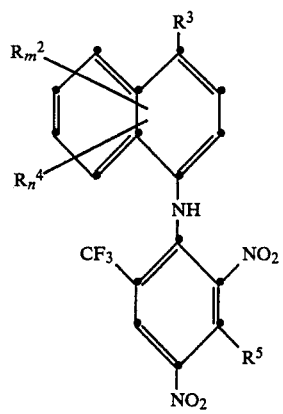

wherein:
$R^2$ is $C_1$-$C_4$ alkyl;
$R^3$ is halogen, $C_1$-$C_4$ fluoroalkyl, $C_1$-$C_4$ fluoroalkoxy or $C_1$-$C_4$ fluoroalkylthio;
$R^4$ is halogen;
$R^5$ is hydrogen or halogen;
m is 0, 1 or 2; and
n is 0 or 1;
with the proviso that, when an $R^4$ substituent exists, it is at other than the 2-position;
(d) a benzenamine selected from 2,4-dinitro-N-[4-(trifluoromethoxy)phenyl]-6-(trifluoromethyl)benzenamine; 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine;
(e) metichlorpindol; or
(f) a pharmaceutically acceptable salt of an (a)-(e) compound.

In formula 4, $C_1$-$C_4$ alkyl includes methyl, ethyl, n-propyl, isopropyl, n-butyl, sec-butyl, isobutyl, tert-butyl, and the like.

The term "halogen" represents fluorine, chlorine, bromine and iodine.

$C_1$-$C_4$ Fluoroalkyl is a $C_1$-$C_4$ alkyl group bearing one or more fluorine atoms. Such fluoroalkyl groups include trifluoromethyl, 1,1,2,2-tetrafluoroethyl, pentafluoroethyl, 1,2,3,3-tetrafluoropropyl, nonafluorobutyl, and the like.

$C_1$-$C_4$ Fluoroalkoxy is a $C_1$-$C_4$ alkoxy group bearing one or more fluorine atoms. Such fluoroalkoxy groups include difluoromethoxy, trifluoromethoxy, 1-fluoroethoxy, 1,1,2,2-tetrafluoroethoxy, pentafluoroethoxy, 1,2,2,3,3-pentafluoropropoxy, heptafluoropropoxy, 4,4,4-trifluorobutoxy, and the like.

$C_1$-$C_4$ Fluoroalkylthio is a $C_1$-$C_4$ alkylthio group bearing one or more fluorine atoms. Such fluoroalkylthio groups include trifluoromethylthio, 1,1,2,2-tetrafluoroethylthio, pentafluoroethylthio, 4,4,4-trifluorobutylthio, and the like.

Preferred formula 4 compounds are those wherein m and n are 0 and $R^5$ is hydrogen.

Typical formula 4 compounds are:

4-Fluoro-N-[2,4-dinitro-6-(trifluoromethyl)phenyl]-1-naphthalenamine

4-Iodo-N-[2,4-dinitro-6-(trifluoromethyl)phenyl]-1-naphthalenamine

4-Trifluoromethyl-N-[2,4-dinitro-6-(trifluoromethyl)-phenyl]-1-naphthalenamine

4-Pentafluoroethyl-N-[2,4-dinitro-6-(trifluoromethyl)-phenyl-1-naphthalenamine 6,7-Dimethyl-4-(1,1,2,2-tetrafluoroethoxy)-N-[2,4-dinitro-6-(trifluoromethyl)phenyl]-1-naphthalenamine 2-Isopropyl-4-chloro-N-[3-chloro-2,4-dinitro-6-(trifluoromethyl)phenyl]-1-naphthalenamine 8-n-Butyl-4-(4,4,4-trifluorobutoxy)-N-[3-bromo-2,4-dinitro-6-(trifluoromethyl)phenyl]-1-naphthalenamine 3-Methyl-6-propyl-4-heptafluoropropyl-N-[2,4-dinitro-6-(trifluoromethyl)phenyl]-1-naphthalenamine 3,4-Dichloro-N-[2,4-dinitro-6-(trifluoromethyl)phenyl]-1-naphthalenamine 4-(1,1-Difluoroethoxy)-N-[2,4-dinitro-6-(trifluoromethyl)phenyl]-1-naphthalenamine 4-(1,1,2,2-Tetrafluoroethoxy)-N-[2,4-dinitro-6-(trifluoromethyl)phenyl]-1-naphthalenamine and 4-(1,1,2,2-Tetrafluoroethylthio)-N-[2,4-dinitro-6-(trifluoromethyl)phenyl]-1-naphthalenamine.

Anticoccidial combinations comprising nicarbazin or 4,4'-dinitrocarbanilide and polyether antibiotics are disclosed by Maurice E. Callender and Thomas K. Jeffers in U.S. Pat. No. 4,218,438, issued Aug. 19, 1980. Anticoccidial combinations of the napthalenamines of formula 4 with polyether antibiotics are disclosed by Albert J. Clinton and George O. P. O'Doherty in copending application Ser. No. 631,665, filed July 17, 1984. Anticoccidial combinations comprising the specified benzenamines and a polyether antibiotic are disclosed by Clinton and O'Doherty in U.S. Pat. No. 4,366,168. A coccidiocidal combination of monensin (a polyether antibiotic) and metichlorpindol is disclosed by Larry R. McDougald in U.S. Pat. No. 4,061,755, issued Dec. 6, 1977.

Nicarbazin and 4,4'-dinitrocarbanilide are taught in U.S. Pat. No. 2,731,382. Nicarbazin is a complex of 4,4'-dinitrocarbanilide and 2-hydroxy-4,6-dimethylpyrimidine, but the 4,4'-dinitrocarbanilide alone exhibits anticoccidial activity. See Science 122, 244 (1955).

The components of the combinations of an A80438 compound with compounds 2(a)-(e) are used in amounts which, in combination, are synergistic as to at least one coccidiosis-causing organism. In general, the maximum amounts to be used in the combinations are the same as the maximum amounts for anticoccidial treatment by the individual components. The lower limits are generally less than that required for therapy by the individual components. Accordingly, the present invention is generally practiced with compositions containing (1) from about 2 to about 100 ppm of an A80438 compound and (2) (a) from about 5 to 125 ppm of nicarbazin, (b) from about 25 to about 150 ppm of 4,4'-dinitrocarbanilide, (c) from about 1 to about 1000 ppm of the specified napthalenamine, (d) from about 5 to about 125 ppm of a specified benzenamine, or (e) from about 20 to about 70 ppm of metichlorpindol. The A-80438 compounds should be particularly effective when administered with nicarbazin. Preferred combinations contain from about 2 to about 20 ppm of an A80438 compound with from about 5 to about 50 ppm of nicarbazin.

Another important property of the A80438 compounds is the ability to improve feed-utilization efficiency in animals. For example, the A80438 compounds improve feed-utilization efficiency in ruminants which have a developed rumen function.

The efficiency of feed use can be monitored by observing the production and concentration of propionate compounds in the rumen using the method described by Arthur P. Raun in U.S. Pat. No. 3,794,732 (see especially Example 5). Table VII shows the ratio of volatile-fatty-acid (VFA) concentrations in A80438-treated flasks to concentrations in control flasks in this test.

TABLE VII

| Effect of A80438 on Ruminant Feed-Utilization Efficiency | | | | |
|---|---|---|---|---|
| | Ratio of Treated to Control Values | | | |
| Dosage mcg/mL | Molar % Propionate | Molar % Acetate | Molar % Butyrate | Total VFA mM/L |
| 5 | 1.519* | 0.892 | 0.582 | 0.934 |
| 1 | 1.367* | 0.921 | 0.710 | 0.919 |
| 0.2 | 1.262* | 0.863 | 0.933 | 1.013 |

*LSD; two-tailed t-test; significant at P < 0.01; $C_3$ > 99 percent upper confidence limit The A80438 compounds are typically effective in increasing propionate and, thereby, the efficiency of feed utilization when administered to ruminants orally at rates of from about 0.02 mg/kg/day to about 1.5 mg/kg/day. Preferable rates of administration are from about 0.05 mg/kg/day to about 0.5 mg/kg/day. A preferred method of administration is to mix the compound with the animals' feed.

This invention further relates to feed compositions adapted to increase feed utilization in ruminant animals comprising feed ration and from 2.5 to 25 grams per ton of an A80438 compound.

As described supra, A80438 compounds are active against anaerobic bacteria, including *Clostridium perfringens*. A80438 compounds should, therefore, be beneficial in the treatment of (which includes prevention of) enteritis in chickens, swine, cattle and sheep. A80438 compounds should also be useful in the treatment of enterotoxemia in ruminants.

In another aspect the A80438 compounds are useful in the treatment of swine dysentery. A80438 inhibits the growth of *Treponema hyodysenteriae*, the causative agent of swine dysentery, at levels less than or equal to 0.39 mcg/ml.

A preferred method of administering an A80438 compound to swine comprises incorporating an effective amount of the compound into the feed ration or drinking water. An appropriate effective amount will depend upon whether the treatment is to prevent dysentery in swine exposed to the disease or to cure swine already infected with the disease. Usually, a lower concentration of active compound is needed to prevent infection than is required to eliminate infection in animals already afflicted. In general, amounts in the range of from about 20 to about 100 grams of A80438 compound per ton of feed are effective to prevent infection. Amounts in the range of from about 50 to about 250 grams of A80438 compound per ton of feed are recommended for treating swine suffering from dysentery. These amounts provide from about 1 to about 5 mg/kg of body weight per day (prophylactic treatment) or from about 2.5 to about 12.5 mg/kg of body weight per day (treatment of infected animal). When added to the drinking water, amounts of from about 0.04 to about 0.2 g (prophylactic) or from about 0.2 to about 1 g (therapeutic) of A80438 compound per gallon of water are recommended.

This invention further relates to feed compositions for treating swine dysentery comprising swine ration and an effective amount of an A80438 compound. As discussed supra, an effective amount is typically one in the range of from about 20 to about 250 grams of A80438 compound per ton of feed.

The A80438 compounds are active against polio virus. For example, tissue-culture tests show that A80438 is active against Polio III virus at a level of 2000 mcg/mL.

Antibiotic A80438 exhibits ion-transport properties and is, therefore, an ionophore (ion-bearer) (see B. C. Pressman in "Inorganic Biochemistry", G. L. Eichhorn, Ed.; Elsevier, New York, 1973; Vol. 1, Chapter 6). At a 0.5 mcg/mL concentration A80438 showed ionophorous activity; its activity with $Na^+$, $K^+$ and $Rb^+$ was better than that with $Cs^+$ or $Li^+$. At a lower concentration (0.2 mcg/mL), A80438 appeared to select $Na^+$ over other alkali-metal cations.

A80438 can be used, therefore, when the selective removal of particular cations is desired. Examples of such uses include the removal and recovery of silver ions from solutions in photography, the removal of toxic cations from industrial waste streams before such streams are discharged to the environment, and desalinization of sea water. A80438 can be used as one component of an ion-specific electrode (see O. Kedem, et al., U.S. Pat. No. 3,753,887, Aug. 21, 1973).

A80438 alters the cation permeability of both natural and artificial membranes. A80438 can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, *Science* 172, 377 (1971)].

In yet another aspect, A80438 is active as an inhibitor of the enzyme ATPase. ATPase, an alkali-metal-sensitive enzyme found in cell membranes, is involved in the energy necessary for active transport. "Active transport" refers to the energy requiring series of operations whereby intracellular and extracellular fluids maintain their compositions. Inhibitors of ATPase reduce the energy required for active transport. In vitro tests have shown that A80438 inhibits a mitochondrial ATPase with a half-effective concentration ($IC_{50}$) of 0.5 mcg/mL.

The A80438 compounds are also potential cardiotonic agents.

The A80438 compounds can be administered to animals orally or parenterally. The most practical way to administer the A80438 compounds is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80438 compound directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid or solid preparations.

The final formulation of feeds for animals will depend upon the amount of drug to be administered. The common methods of formulating, mixing, an pelleting feeds may be used to prepare feeds containing an A80438 compound.

The A80438 compounds may be formulated for parenteral administration by methods recognized in the veterinary pharmaceutical art. Effective injectable compositions containing the A80438 compounds may be in either suspension or solution form. In the solution form, the A80438 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In order to illustrate more fully the operation of this invention, the following examples are provided:

EXAMPLE 1

Preparation of Antibiotic A80438 Using *Streptomyces bobili*

A. Shake-flask Fermentation of *Streptomyces bobili*

The culture *Streptomyces bobili* NRRL 15971, either as a lyophilized pellet or as a suspension maintained in liquid nitrogen, is used to inoculate a vegetative medium having the following composition:

| Vegetative or Seed Medium | |
|---|---|
| Ingredient | Amount (g/L) |
| Glucose | 15 |
| Potato Dextrin | 10 |
| $Na_2SO_4$ | 2 |
| Pancreatic Digest of Casein* | 5 |
| Yeast Extract | 5 |

-continued

| Vegetative or Seed Medium | |
|---|---|
| Ingredient | Amount (g/L) |
| Tap water | q.s. 1 liter |

*Bacto Tryptone (Difco Laboratories, Detroit, Mich.)

Slants or plates are prepared by adding 2.5% agar to the seed medium. The inoculated slant is incubated at 30° C. for from about 10 to about 14 days. The mature slant culture is scraped with a sterile tool to loosen the spores and remove and macerate the mycelial mat. About one-fourth of the loosened spores and culture growth thus obtained is used to inoculate 50 mL of a first-stage seed medium.

The inoculated first-stage medium is incubated in a 250-mL Erlenmeyer flask at 30° C. for about 72 hours on a shaker orbiting in a two-inch (5.08 cm) circle at 250 rpm.

This incubated first-stage medium (1.25 mL) is used to inoculate 50 mL of a production medium having the following composition:

| Ingredient | Amount (g/L) |
|---|---|
| Glucose | 40.0 |
| Soybean flour | 7.5 |
| Enzyme-hydrolyzed casein* | 3.0 |
| $Na_2SO_4$ | 2.0 |
| $CaCO_3$ | 2.0 |
| Tap water | q.s. 1 liter |

*Amber EHC (Amber Laboratories, Juneau, Wisc.)

The inoculated production medium is incubated in a 250-mL wide-mouth Erlenmeyer flask at 30° C. for 8 to 10 days on a shaker orbiting in a two-inch circle at 250 rpm.

B. Tank Fermentation of *Streptomyces bobili*

In order to provide a large volume of inoculum, 10 mL of incubated first-stage medium, prepared as described in Section A, is used to inoculate 400 mL of a second-stage growth medium having the same composition as that of the first-stage medium. This second-stage vegetative medium is incubated in a two-liter wide-mouth Erlenmeyer flask for about 48 hours at 30° C. on a shaker orbiting in a two-inch circle at 250 rpm.

Incubated second-stage vegetative medium (400 mL) thus prepared is used to inoculated 100 liters of sterile production medium, prepared as described in Section A. The inoculated production medium is allowed to ferment in a 165-liter stirred fermentation tank for 8 to 10 days at a temperature of 30° C. Low airflow (0.12–0.25 v/v/m) and low rpm (150–200) in the stirred vessel maintain a dissolved oxygen level above 30% of air saturation.

EXAMPLE 2

Isolation of A80438 produced by *Streptomyces bobili*

Whole fermentation broth (200 L) containing 3% Hyflo Supercel was filtered through a filter press. The mycelial cake was extracted twice by circulating methanol (50–60 L) through the press.

This extract was concentrated under vacuum to remove the methanol. The resulting aqueous solution (38 L), adjusted to pH 8 with NaOH, was extracted twice with ethyl acetate (⅓ volume).

The broth filtrate, adjusted to pH 8 with NaOH, was extracted twice with ethyl acetate (⅓ volumes). The ethyl acetate extracts were combined and concentrated under vacuum to a volume of 1 L.

The broth and mycelial ethyl acetate extracts were combined and concentrated under vacuum to a volume of 1 L.

Extracts obtained by this procedure from 400 L of whole fermentation broth were combined and concentrated under vacuum to an oily residue. The residue, dissolved in toluene (400 mL), was applied to a column containing silica gel (Woelm, 2 L) packed in toluene. The column was developed sequentially with toluene (6 L) and toluene:ethyl acetate mixtures [9:1 (6 L), 4:1 (8 L) and 3:2 (4 L)]. Fractions having a volume of 1 L were collected during elution of the first 12 L, and 500-ml fractions were collected thereafter. Elution was followed by (1) bioassay using *Bacillus subtilis* and (2) silica gel TLC (Merck plates), using a toluene:ethanol (4:1) solvent system and vanillin-$H_2SO_4$ spray for detection. Fractions containing A80438 [from the toluene:ethyl acetate (4:1) eluate] were combined and concentrated under vacuum to a volume of 80 mL.

A portion of this concentrate (10 mL) was applied to a column containing 70 mL of silica gel (Woelm 100–200) packed in toluene. This column was developed sequentially with toluene:ethyl acetate (9:1, 4:1, and 3:2), collecting 10-mL fractions. Elution was monitored by TLC. Fractions containing A80438 were combined and concentrated under vacuum to dryness. The residue was dissolved in a small quantity of dioxane; water (¼ volume) was added; and the solution was freeze-dried to give 257 mg of amorphous A80438 as a powder. The powder was dissolved in acetone (3.5 mL); water (1.5 mL) was added; and the mixture was allowed to stand at 5° C. overnight. The crystals which formed were separated by filtration, washed with acetone:water (1:1) and dried under vacuum to give 233 mg of crystalline A80438.

EXAMPLE 3

Preparation of Antibiotic A80438 Using *Streptomyces pactum*

A. Shake-flask Fermentation of *Streptomyces pactum*

The culture *Streptomyces pactum* NRRL 15970, either as a lyophilized pellet or as a suspension maintained in liquid nitrogen, is used to inoculate an agar slant having the following composition:

| Agar Slant Medium | |
|---|---|
| Ingredient | Amount (g/L) |
| Glucose | 2.5 |
| Soluble Starch | 5.0 |
| Yeast Extract | 1.25 |
| Enzyme-hydrolyzed Casein* | 1.25 |
| $CaCO_3$ | 0.25 |
| Agar | 15.0 |
| Deionized Water | q.s. to 1 liter |

Unadjusted pH = 6.3; adjust to pH 7.5 with NaOH; pH after sterilization = 6.9
*N—Z Amine A, Humko-Sheffield Chemical, Lyndhurst NJ The inoculated slant is incubated at 30° C. for from about 10 to about 14 days. The mature slant culture is scraped with a sterile tool to loosen the spores and remove and macerate the mycelial mat. About one-fourth of the loosened spores and culture growth thus obtained is used to inoculate 50 mL of a first-stage vegetative medium having the following composition:

| Vegetative Medium | |
|---|---|
| Ingredient | Amount (g/L) |
| Glucose | 10 |
| Soluble Starch | 20 |
| Enzyme-hydrolyzed Casein* | 5 |
| Yeast Extract | 5 |
| CaCO3 | 1 |
| Tap water | q.s. 1 liter |

Unadjusted pH = 6.6; adjust to pH 7.2 with NaOH; pH after sterilization = 6.8
*N—Z Amine A The inoculated first-stage medium is incubated in a 250-mL Erlenmeyer flask at 30° C. for about 48 hours on a shaker orbiting in a two-inch (5.08 cm) circle at 250 rpm.

This incubated first-stage medium (1.25 mL) is used to inoculate 50 mL of a production medium having the following composition:

| Ingredient | Amount |
|---|---|
| Glucose | 20 g/L |
| Blackstrap Molasses | 20 g/L |
| Peptone* | 5 g/L |
| CaC03 | 2 g/L |
| Czapek's Mineral Stock** | 2 mL |
| Deionized water | q.s. 1 liter |

*Bacto Peptone (Difco Laboratories, Detroit MI)
**Czapek's Mineral Stock has the following composition:
KCl        10%
MgSO4.7H2O  10%
FeSO4.7H2O  0.2% (dissolved in 2 ml of conc. HCl)
Deionized water  q.s. to 1 liter The inoculated production medium is incubated in a 250-mL wide-mouth Erlenmeyer flask at 30° C. for 8 to 10 days on a shaker orbiting in a two-inch circle at 250 rpm.

B. Tank Fermentation of *Streptomyces pactum*

In order to provide a large volume of inoculum, 10 mL of incubated first-stage medium, prepared as described in Section A, is used to inoculate 400 mL of a second-stage growth medium having the same composition as that of the first-stage medium. This second-stage vegetative medium is incubated in a two-liter wide-mouth Erlenmeyer flask for about 48 hours at 30° C. on a shaker orbiting in a two-inch circle at 250 rpm.

Incubated second-stage vegetative medium (400 mL) thus prepared is used to inoculate 100 liters of sterile production medium, prepared as described in Section A. The inoculated production medium is allowed to ferment in a 165-liter stirred fermentation tank for 6 to 8 days at a temperature of 30° C. Low airflow (0.125 v/v/m) and low rpm (150-175) in the stirred vessel maintain a dissolved oxygen level above 30% of air saturation.

EXAMPLE 4

Isolation of A80438 Produced by *Streptomyces pactum*

Whole fermentation broth (114 L), prepared as described in Example 3 and mixed with Hyflo Supercel (3%), was adjusted to pH 3.0 with HCl and filtered through a filter press. The mycelial cake was extracted twice in the press with a solution (30 L) of methanol:water (9:1) containing 1% NaHCO3. The methanol extracts were combined (60 L), concentrated under vacuum to a volume of 14 L, and adjusted to pH 8.5 with NaOH. The concentrate was extracted twice with ethyl acetate (½ volumes), and the combined extracts (12 L) were concentrated under vacuum to a volume of 0.6 L.

Concentrates obtained in this manner from three 100-L fermentations were combined and evaporated to dryness under vacuum. The residue, dissolved in CHCl3 (200 ml), was applied to a 6-×40-cm column of silica gel (1 L, Woelm 100-200 μm) packed in CHCl3. The column was eluted with CHCl3 (6 L) and CHCl3:EtOAc [49:1 (1 L) and 9:1 (4 L)]. Elution was monitored by TLC and bioassay. Fractions containing A80438 were combined and concentrated under vacuum to dryness.

The residue thus obtained, dissolved in acetone (150 mL), was applied to small amount of silica gel (Woelm 100-200 μm) and dried. The silica gel containing A80438 was then applied to a 6-×40-cm column containing silica gel (1 L, Woelm 100-200 μm) packed in CHCl3. The column was developed sequentially with CHCl3 (6 L) and CHCl3:EtOAc [9:1 (5 L) and 4:1 (2 L)]. Elution was monitored by TLC and bioassay. Fractions containing A80438 were combined and concentrated under vacuum to dryness. The residue obtained was crystallized from acetone to give 14.27 g of crystalline A80438 as the sodium salt.

EXAMPLE 5

Preparation A80438 Free Acid from A80438 Na

A80438 sodium salt (1 g) was dissolved in acetone (5 mL); water (25 mL) was added; and the pH of this solution was adjusted to 3.0 with 1N HCl. Water (25 mL) was added, and a gummy precipitate formed. The mixture was extracted twice with ethyl acetate (100 mL each). The combined extracts were evaporated under vacuum to dryness. The residue was dissolved in acetone (50 mL), and water (25 mL) was added. The mixture again was allowed to stand at room temperature until the gummy precipitate formed. The precipitate was separated and dissolved in warm pentane (100 mL). The pentane solution was allowed to stand at room temperature. The pentane was then decanted and evaporated under vacuum to give 849 mg of A80438 in the acid form (mp 55°-56° C.) as a white powder.

EXAMPLE 6

Preparation of A80438 Potassium Salt

A80438 (acid form, 400 mg) was dissolved in acetone (50 mL); water (25 mL) was added; and the pH was adjusted to 10.0 with 1N KOH. Water (25 mL) was added, and the mixture was stirred for 15 minutes, maintaining the pH at 10. The mixture was then extracted twice ethyl acetate (100 mL each), and the combined extracts were evaporated under vacuum under dryness. The residue was dissolved in acetone (50 mL); water (50 mL) was added; and the mixture was allowed to stand at room temperature overnight. The crystals which formed were separated by filtration, washed with water and dried in a vacuum oven at 50° C. to give 179 mg of A80438 potassium salt (mp 157°-159° C.).

We claim:
1. Antibiotic A80438 which has the formula

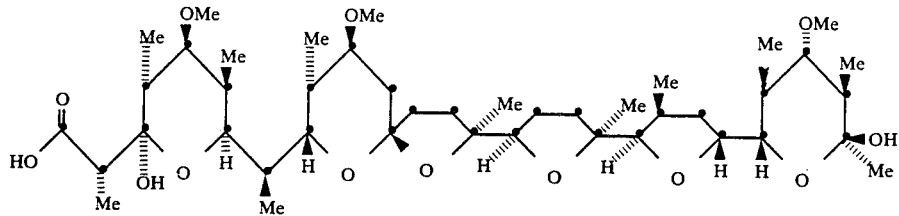

the $C_1-C_7$-alkanoyl and $C_1-C_7$-alkyl ester and $C_1-C_7$ alkyl ether derivatives of A80438, and the pharmaceutically acceptable salts of A80438 and of the specified ester and ether derivatives.

2. A compound of claim 1 which is antibiotic A80438 or a salt of A80438.

3. A compound of claim 1 which is a $C_1-C_6$-alkanoyl ester derivative of A80438 or a salt of this compound.

4. The compound of claim 3 which is the acetyl derivative of A80438.

5. The compound of claim 3 which is the propionyl derivative of A80438.

6. A compound of the formula

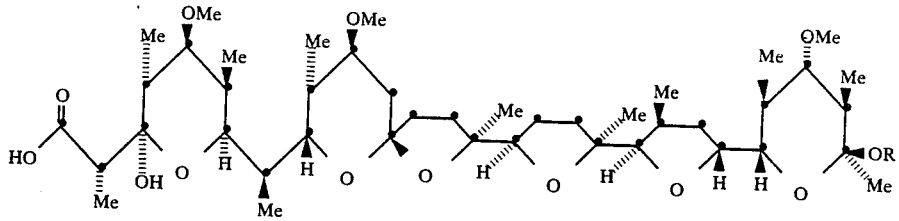

wherein R is —CONHR$_1$ and R$_1$ is alkyl, aryl, alkylaryl, arylalkyl, halo-aryl, nitro-aryl, haloaryl-alkyl, alkoxyaryl, aryloxyaryl, arylcycloalkyl, acyl-aryl and cycloalkyl wherein alkyl contains 1–7 carbon atoms; aryl is selected from the group phenyl, pyridyl or furyl, alkoxy contains 1 to 7 carbon atoms and cycloalkyl contains 3 to 7 carbon atoms; or a pharmaceutically acceptable salt thereof.

7. A compond of claim 6 wherein R$_1$ is $C_1-C_7$-alkyl.

8. A compound of claim 7 wherein R$_1$ is methyl.

9. A method for increasing feed-utilization efficiency in ruminant animals which comprises orally administering to the animal an effective propionate-increasing amount of a compound of claim 1.

10. The method of claim 9 wherein the compound is A80438 or a pharmaceutically acceptable salt of A80438.

11. The method of claim 9 wherein the compound is a $C_2-C_6$-alkanoyl ester derivative of A80438 or a pharmaceutically acceptable salt of the derivative.

12. The method of claim 9 wherein the compound is a $C_1-C_4$-alkyl ether derivative of A80438 or a pharmaceutically acceptable salt of the derivative.

13. A method for increasing feed-utilization efficiency in ruminant animals which comprises orally administering to the animal an effective propionate-increasing amount of a compound of claim 6.

14. A method of claim 13 wherein the compound is one in which R$_1$ is $C_1-C_7$-alkyl.

15. A feed composition for increasing feed utilization efficiency in ruminant animals comprising animal feed and an effective amount of a compound of claim 1.

16. A feed composition for increasing feed utilization efficiency in ruminant animals comprising animal feed and an effective amount of a compound of claim 6.

17. A method for treating coccidiosis in poultry which comprises administering to poultry an effective amount of a compound of claim 1.

18. The method of claim 17 wherein the compound is A80438 or a pharmaceutically acceptable salt of A80438.

19. The method of claim 17 wherein the compound is a $C_2-C_6$-alkanoyl ester derivative of A80438 or a pharmaceutically acceptable salt of the derivative.

20. The method of claim 17 wherein the compound is a $C_1-C_4$-alkyl ether derivative of A80438 or a pharmaceutically acceptable salt of the derivative.

21. A method for treating coccidiosis in poultry which comprises administering to poultry an effective amount of a compound of claim 6.

22. A feed composition for treating coccidiosis comprising animal feed and an amount of a compound of claim 1 which is effective for controlling coccidiosis.

23. A composition of claim 22 wherein the compound is A80438 or a pharmaceutically acceptable salt of A80438.

24. A feed composition for treating coccidiosis comprising animal feed and an amount of a compound of claim 6 which is effective for controlling coccidiosis.

25. A method for treating coccidiosis in poultry which comprises administering to the poultry a feedstuff comprising a first component which is a compound of claim 1 and a second component which is selected from the group consisting of (a) nicarbazin,
(b) 4,4'-dinitrocarbanilide,
(c) a naphthalenamine of the formula

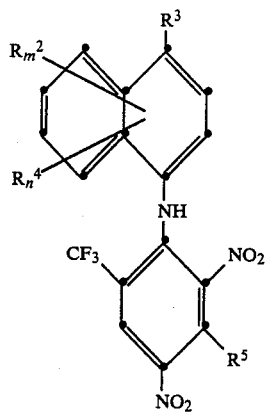

wherein:
R² is C₁–C₄ alkyl;
R³ is halogen, C₁–C₄ fluoroalkyl, C₁–C₄ fluoroalkoxy or C₁–C₄ fluoroalkylthio;
R⁴ is halogen;
R⁵ is hydrogen or halogen;
m is 0, 1 or 2; and
n is 0 or 1;
with the proviso that, when an R⁴ substituent exists, it is at other than the 2-position;

(d) a benzenamine selected from 2,4-dinitro-N-[4-(trifluoromethoxy)phenyl]-6-(trifluoromethyl)benzenamine, 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine;

(e) metichlorpindol; or (f) a pharmaceutically acceptable salt of an (a)–(e) compound;

the components being present in the feedstuff in amounts which, in combination, are synergistic as to at least one coccidiosis-causing strain of Eimeria.

26. A poultry feedstuff composition comprising a first component which is a compound of claim 1 and a second component which is selected from the group consisting of (a) nicarbazin,
(b) 4,4'-dinitrocarbanilide,
(c) a naphthalenamine of the formula

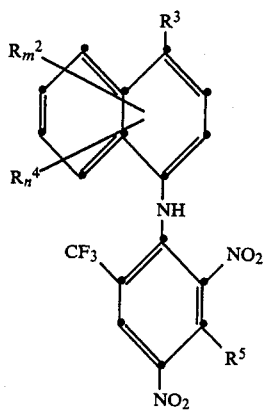

wherein:
R² is C₁–C₄ alkyl;
R³ is halogen, C₁–C₄ fluoroalkyl, C₁–C₄ fluoroalkoxy or C₁–C₄ fluoroalkylthio;
R⁴ is halogen;
R⁵ is hydrogen or halogen;
m is 0, 1 or 2; and
n is 0 or 1;
with the proviso that, when an R⁴ substituent exists, it is at other than the 2-position;

(d) a benzenamine selected from 2,4-dinitro-N-[4-(trifluoromethoxy)phenyl]-6-(trifluoromethyl)benzenamine, 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine;

(e) metichlorpindol; or (f) a pharmaceutically acceptable salt of an (a)–(e) compound;

the components being present in the feedstuff in amounts which, in combination, are synergistic as to at least one coccidiosis-causing strain of Eimeria.

27. A poultry feedstuff composition comprising a first component which is a compound of claim 6 and a second component which is selected from the group consisting of (a) nicarbazin,
(b) 4,4'-dinitrocarbanilide,
(c) a naphthalenamine of the formula

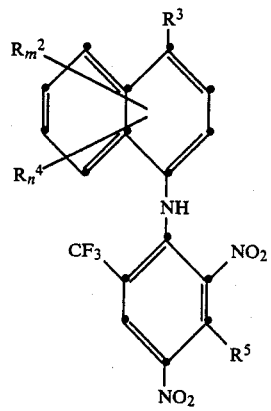

wherein:
R² is C₁–C₄ alkyl;
R³ is halogen, C₁–C₄ fluoroalkyl, C₁–C₄ fluoroalkoxy or C₁–C₄ fluoroalkylthio;
R⁴ is halogen;
R⁵ is hydrogen or halogen;
m is 0, 1 or 2; and
n is 0 or 1;
with the proviso that, when an R⁴ substituent exists, it is at other than the 2-position;

(d) a benzenamine selected from 2,4-dinitro-N-[4-(trifluoromethoxy)phenyl]-6-(trifluoromethyl)benzenamine, 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine;

(e) metichlorpindol; or (f) a pharmaceutically acceptable salt of an (a)-(e) compound;

the components being present in the feedstuff in amounts which, in combination, are synergistic as to at least one coccidiosis-causing strain of Eimeria.

28. A method for treating swine dysentery which comprises administering to swine an effective amount of a compound of claim 1 for treating dysentery.

29. A method for treating swine dysentery which comprises administering to swine an effective amount of a compound of claim 6 for treating dysentery.

30. A feed composition for treating swine dysentery comprising animal feed and an effective amount of a compound of claim 1 for treating dysentery.

31. A feed composition for treating swine dysentery comprising animal feed and an effective amount of a compound of claim 6 for treating dysentery.

* * * * *